US006620967B1

(12) United States Patent
Kobayashi

(10) Patent No.: US 6,620,967 B1
(45) Date of Patent: Sep. 16, 2003

(54) KETOSIS-TREATING AGENT

(75) Inventor: Hisamine Kobayashi, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/690,016

(22) Filed: Oct. 17, 2000

(30) Foreign Application Priority Data

Oct. 18, 1999 (JP) .......................................... P11-294931

(51) Int. Cl.$^7$ ........................ A01N 37/18; A61K 38/00; C07C 227/00
(52) U.S. Cl. ......................... 562/433; 562/516; 514/2; 424/439; 426/2; 436/128; 560/178
(58) Field of Search ................................ 562/433, 516; 424/439; 426/2; 436/128; 560/178; 514/2

(56) References Cited

U.S. PATENT DOCUMENTS 4,298,601 A  * 11/1981  Howard ...................... 424/128

FOREIGN PATENT DOCUMENTS

GB         2157561 A  * 10/1985  ......... A61K/31/455

OTHER PUBLICATIONS

Hall et al., J. Lipid Research 25, 1184–1194 (1984).*
Cersosimo et al., Glutamine blocks liposis andketogenesis of fasting. Am J. Physiol. 250, E248–E252, 1986.*

* cited by examiner

Primary Examiner—Christopher S. F. Low
Assistant Examiner—Chih-Min Kam
(74) Attorney, Agent, or Firm—Oblon, Spivak, McClelland, Maier & Neustadt, P.C.

(57) ABSTRACT

A ketosis-treating agent comprising, as an active ingredient, at least one amino acid selected from valine, isoleucine, serine, glutamine and glutamic acid, or a peptide or protein comprising at least one amino acid selected from valine, isoleucine, serine, glutamine and glutamic acid; a method for treating or preventing ketosis, comprising administering to a human or animal an effective amount of the above agent; and a method for treating or preventing symptoms relating to ketone bodies, comprising administering to a human or animal an effective amount of the above agent.

4 Claims, 8 Drawing Sheets

KETOSIS-TREATING AGENT

BACKGROUND OF THE INVENTION

1. Filed of the Invention

The present invention relates to a ketosis-treating agent. Particularly, it relates to a ketosis-treating agent which shows little influence on glucose metabolism and/or has a long duration of its effect.

2. Brief Description of the Background Art

Mobilization of free fatty acids from fatty tissue increases at diabetes, starvation, physical exercise, external injury, surgical operation, attack of fever, or the like, so that fatty acid oxidation in the liver is accelerated because of decrease of utilization of sugars, deficiency of insulin, stress, and the like. As a result, formation of ketone bodies, which is the general term for acetoacetic acid, 3-hydroxybutyric acid and acetone, increases. When the formation of ketone bodies exceeds the capacity of treating it, the ketone bodies are accumulated in blood to cause ketonemia. Conditions where the concentration of ketone bodies is high in urine are called ketonuria, and both of them are called generally ketosis. Since acetoacetic acid and 3-hydroxybutyric acid are strong acids of a medium level, in the case where accumulation of ketone bodies exceeds the buffering capacity of a living body, metabolic acidosis is caused and the living body falls into a fatal state called ketoacidosis. For example, excessive formation of ketone bodies for a long period, of time such as diabetes causes ketoacidosis to finally result in death.

Generally, in order to prevent or treat ketosis, insulin or a sugar, such as glucose or the like, is administered. However, as discussed above, glucose metabolism is disordered in many cases of falling into ketosis so that there is a problem that a blood glucose value largely varies by such administration of insulin or a sugar.

Furthermore, in ruminants, as a result that 3-hydroxybutyric acid is formed from butyric acid that is a fermentation product in the digestive tract, the concentration of ketone bodies in blood even at a physiological state is higher than in non-ruminants, and therefore, the incidence of ketosis in ruminants is high. Especially in milk cows, excessive milk secretion causes imbalance of metabolism with improvement of the milk-secreting ability so that the incidence rate of ketosis is as high as about 10%. Moreover, there is a problem that subclinical ketosis, which does not show remarkable clinical symptoms but accompanies an increase of internal ketone bodies, is increasing and affects the milk secretion and the incidence of other metabolic diseases.

Ketosis is generally treated by intravenous administration of a solution of a sugar, such as glucose, xylitol, or the like, but the effect on reduction of the concentration of ketone bodies is transitory and lasts only a short period of time. Therefore, continuous intravenous injection is required. However, since intravenous administration for a long period of time is extremely difficult, there arises a problem that it is usually required to repeat such single administration frequently (Metabolic Diseases of Cattle (Usi no Taishasei Sikkan), Gakusosha, p. 36).

On the other hand, there are reports on the effects of alanine, aspartic acid and glutamine upon reduction of the concentration of ketone bodies in blood in vivo (Romano Nosadini, *Biochem. J.*, 190:323–332 (1980); Eugenio Cersosimo, *Am. J. Ohysiol.*, 250:E248–E252 (1986)). Especially, the mechanism of reducing ketone bodies in blood was precisely examined on alanine, and it is suggested that it inhibits the formation of acetoacetic acid from acetyl CoA produced by fatty acid oxidation. Furthermore, a similar mechanism has been considered for aspartic acid. However, in these amino acids, there also exists a problem that, in single administration, the effect on reduction of the concentration of ketone bodies is transitory and lasts only a short period of time. Also, as for glutamine, only action of reducing the concentration of ketone bodies at continuous administration was reported, but the presence of the effect on reduction of ketone bodies at single administration and the durability of the effect are not known.

SUMMARY OF THE INVENTION

An object of the present invention is to provide a ketosis-treating agent which does not increase a blood glucose value and shows extremely little influence on glucose metabolism, in view of the circumstances that there are many cases where glucose metabolism is disordered in a ketosis state as described above.

A further object of the present invention is to provide a ketosis-treating agent which does not require frequent administration and has long duration of the effect.

The present invention relates to a ketosis-treating agent comprising, as an active ingredient, at least one amino acid selected from valine, isoleucine, serine, glutamine and glutamic acid, or a peptide or protein comprising at least one amino acid selected from valine, isoleucine, serine, glutamine and glutamic acid.

Furthermore, the present invention relates to a method for treating or preventing ketosis, comprising administering to a human or animal an effective amount of the above agent.

Moreover, the present invention relates to a method for treating or preventing symptoms relating to ketone bodies, comprising administering to a human or animal an effective amount of the above agent.

DETAILED DESCRIPTION OF THE INVENTION

Figure 1:
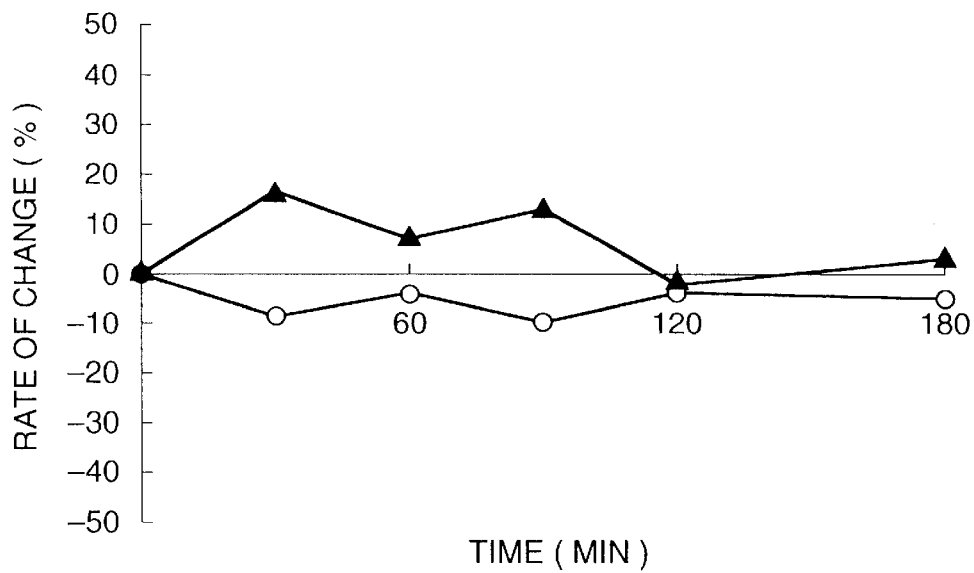
FIGS. 1 to 10 show changes of the concentrations of 3-hydroxybutyric acid and glucose in blood in Example 1.

As a result of intensive studies for solving the above-described problems, the present inventors have found that valine, isoleucine, or serine is effective as a ketosistreating agent which does not increase a blood glucose value and shows extremely little influence on glucose metabolism as the first embodiment.

Also, they have found that valine, isoleucine, glutamine, or glutamic acid is effective as a ketosistreating agent which has long duration of the effect as the second embodiment.

The amino acids used in the first embodiment include valine, isoleucine, and serine, and, in view of long duration of the effect, valine and isoleucine are particularly preferred.

The amino acids used in the second embodiment include valine, isoleucine, glutamine and glutamic acid, and, in view of no increase of a blood glucose value and extremely little influence on glucose metabolism, valine and isoleucine are particularly preferred.

Furthermore, in the present invention, a peptide or protein comprising at least one amino acid among these as a component can be used, and a composition comprising at least one selected from these amino acids, peptides and proteins can also be used.

In the present invention, among the amino acids, peptides and proteins, the amino acids and peptides are more preferred, from the viewpoint of an immediate effect and capability in administering a large amount of the objective substance. Among these, the amino acids are most preferred.

The peptides and proteins used in the present invention, including amino acid numbers, molecular weights, properties and the like, are not particularly limited so long as they include at least one amino acid selected from valine, isoleucine, serine, glutamine and glutamic acid, but they are preferably peptides or proteins which can release the amino acids used in the present invention in a living body after the administration. Also, other amino acids constituting the peptides and proteins are not particularly limited.

The amino acids used in the present invention include usual amino acids, such as those used for pharmaceuticals, livestock feed, food, and the like.

A method for administering the ketosis-treating agent of the present invention is not particularly limited, and it may be administered according to a medical or veterinary medical method as a medicament, a food, or a feed, or as a mixture thereof, optionally together with a carrier, diluent, additive or the like.

Examples of the medicament of the present invention include tablets, powders, granules, fine particles, solutions, and the like. Such a preparation can be produced by making the ketosis-treating agent of the present invention and a pharmaceutically acceptable carrier, diluent, additive or the like into desired forms in the conventional way.

The ketosis-treating agent of the present invention can be applied to foods or feeds effectively. Examples of the foods or feeds containing the ketosis-treating agent include those which can be ingested immediately as such, are ingested after carrying out cooking and the like, and are premixed materials for use in food or feed production.

The dose and frequency of the administration vary depending on the symptoms of ketosis, but generally, it is preferred to administer the ketosis-treating agent at an amount of 20 to 500 mg as amino acids per kg of body weight, once per one to three days.

The ketosis-treating agent of the present invention is administered to a living body in order to reduce the concentration of ketone bodies in a body fluid, such as blood, urine, milk, or the like, or in a living body, or to prevent the increase of the concentration of ketone bodies, and includes those administered for the purpose of improving, treating or preventing various symptoms relating to ketone bodies in a living body.

Examples of the various symptoms relating to ketone bodies include starvation, diabetes, hepatophosphorylase deficiency, acetonemic vomiting, fructose-bisphosphatase deficiency, congenital disorder of organic acid metabolism (e.g., methylmalonic acidemia, propionic acidemia, isovaleric acidemia, hyperlactacidemia, etc.), 3-ketoacid-CoA transferase deficiency, and the like.

The present invention provides a ketosis-treating agent which is easy to control due to little influence on glucose metabolism and is administered less frequently due to long duration of the effect.

The present invention will be explained below based on Examples; however, the present invention is not limited thereto.

EXAMPLE 1

Effects at Oral Administration

Wistar male rats of 6 to 8 week age were subjected to ketosis under starvation for 48 hours and then used for experiment. Each of glutamine, glutamic acid, valine, isoleucine and serine was dissolved in water for injection and administered into the stomach using a gastroconductor to give a dose of 1 or 2 mmol/kg-body weight. As controls, the same quantity of water for injection was similarly administered, or each of glucose and alanine was similarly administered to give a dose of 1 or 2 mmol/kg-body weight.

Before the administration, and 30, 60, 90, 120, 180 and 240 minutes after the administration, blood was collected from a tail vein and the concentration of glucose in blood and the concentration of 3-hydroxybutyric acid usually measured for diagnosis of ketosis were measured.

Figure 2:
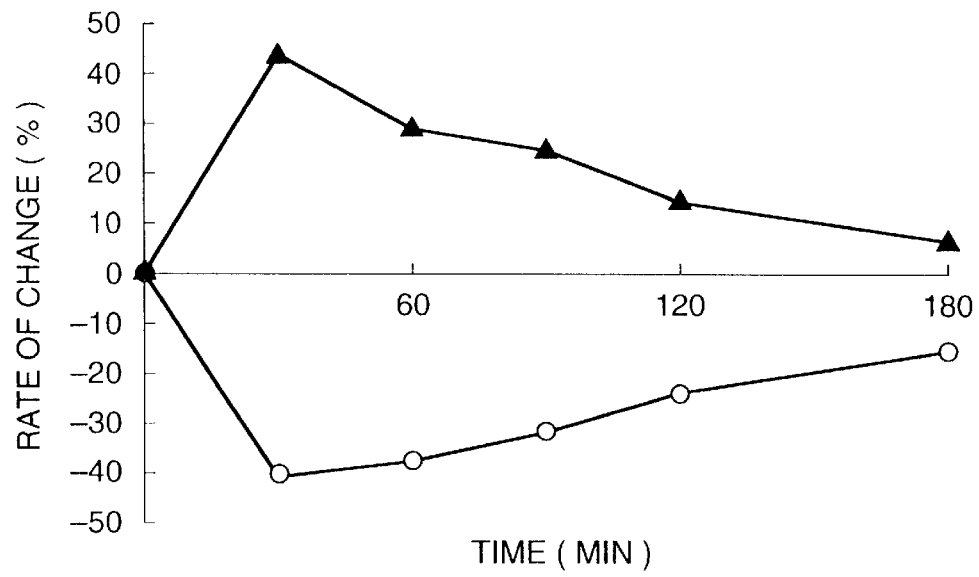
Figure 3:
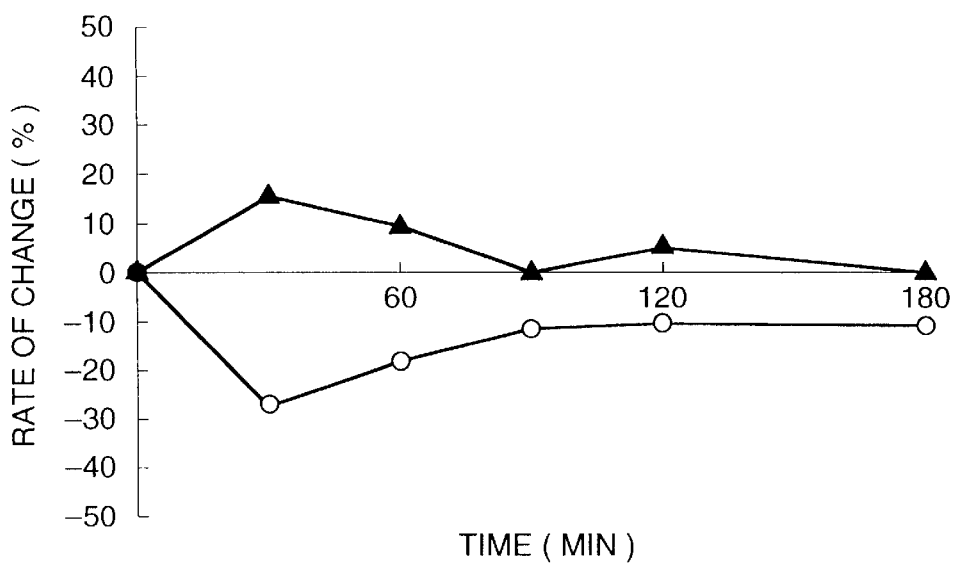
Figure 4:
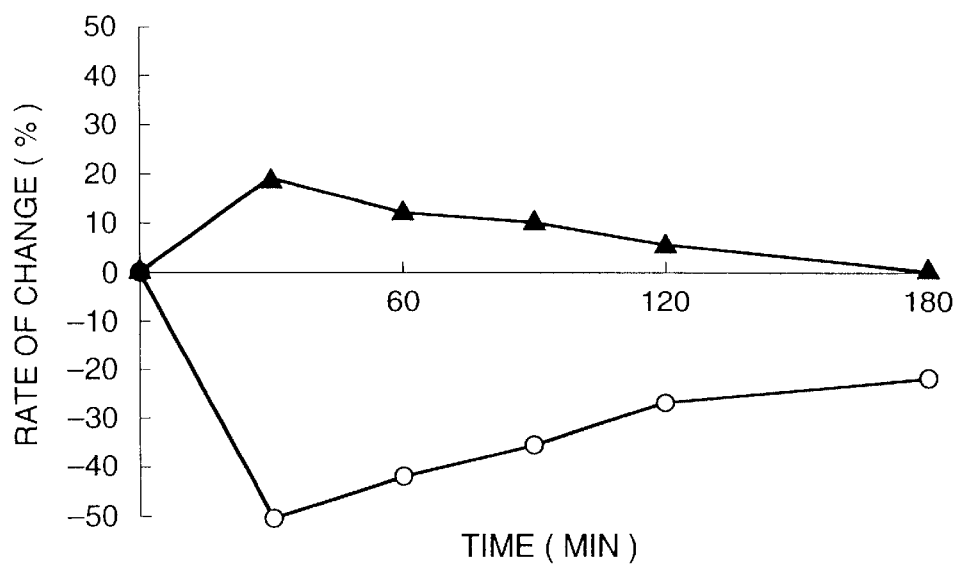
Figure 5:
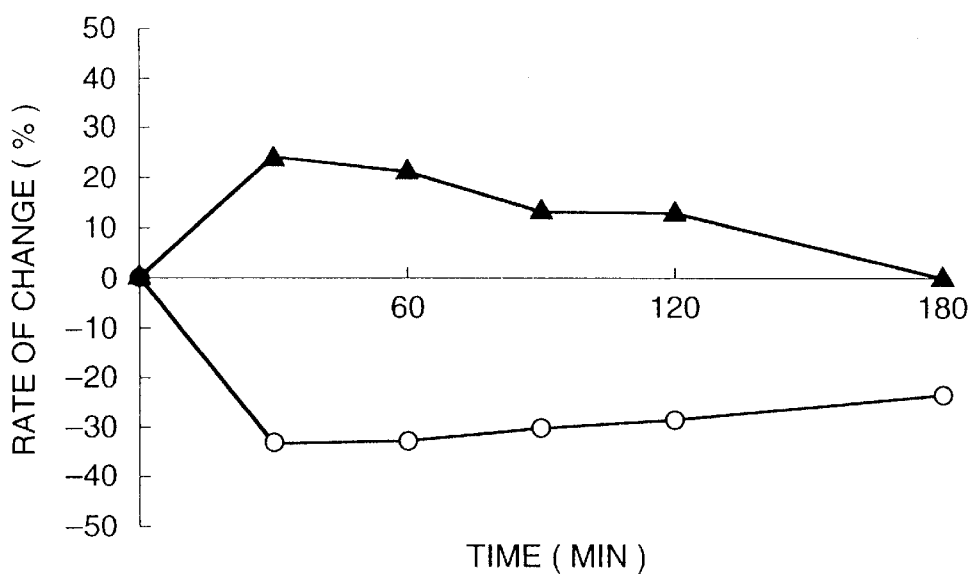
Figure 6:
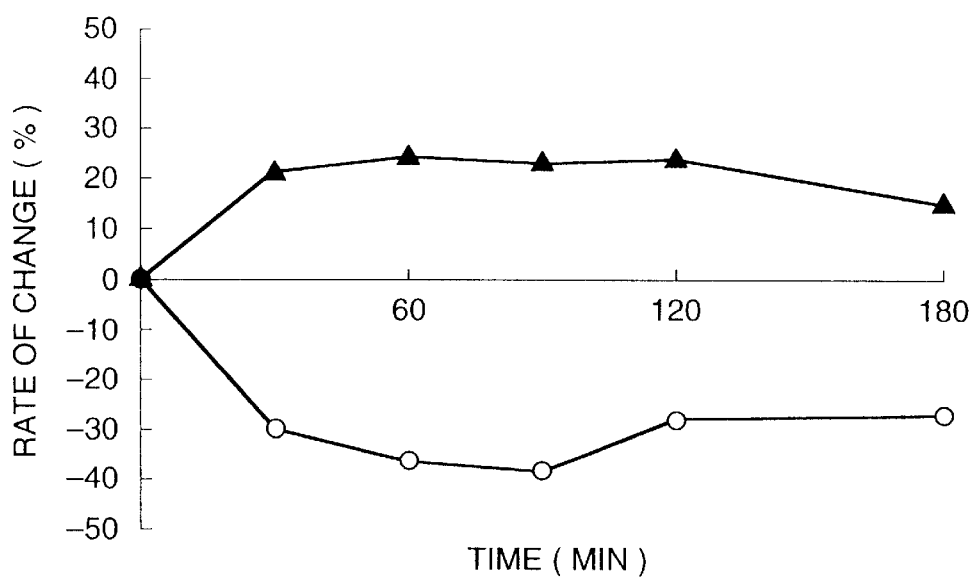
Figure 7:
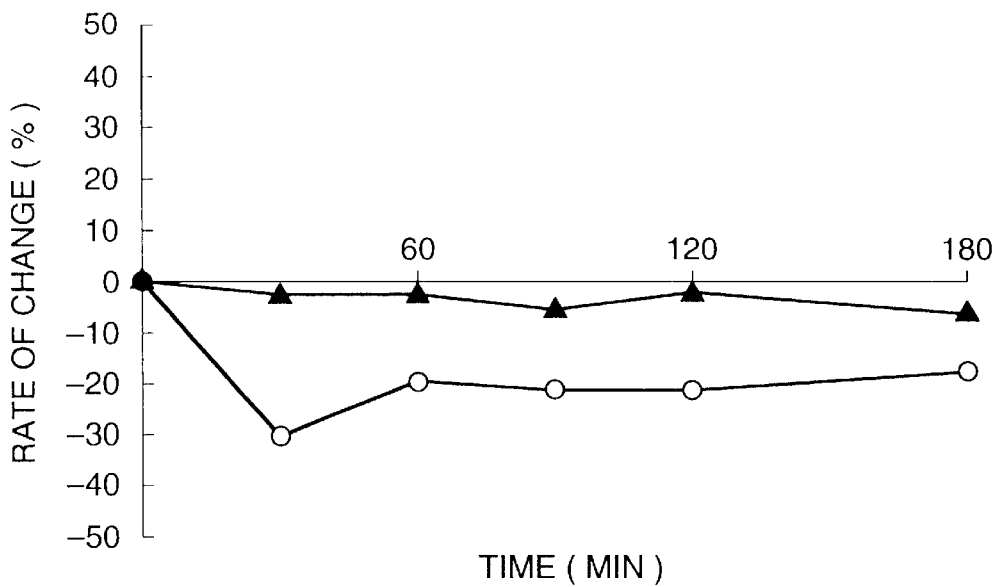
Figure 8:
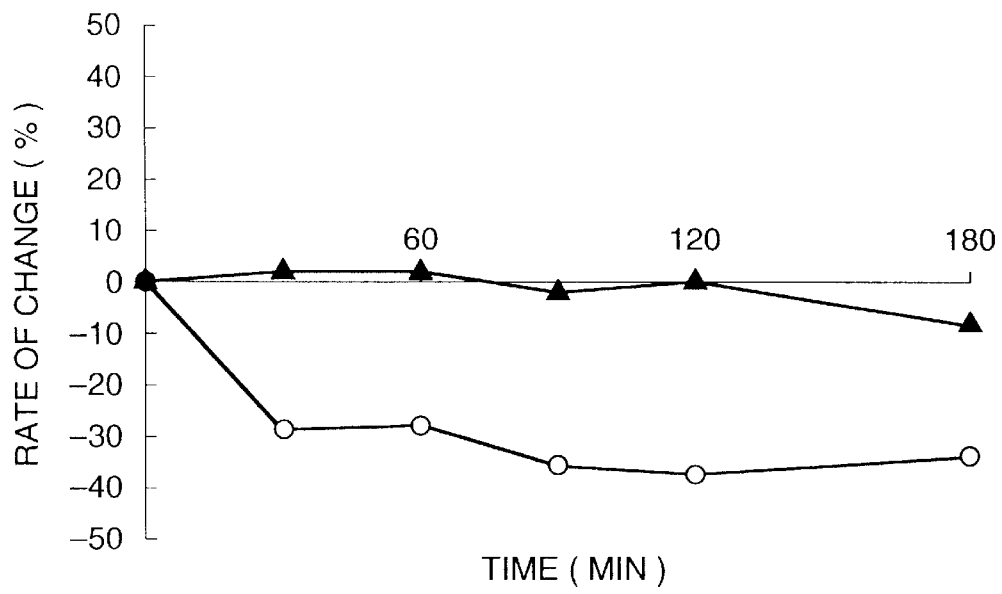
Figure 9:
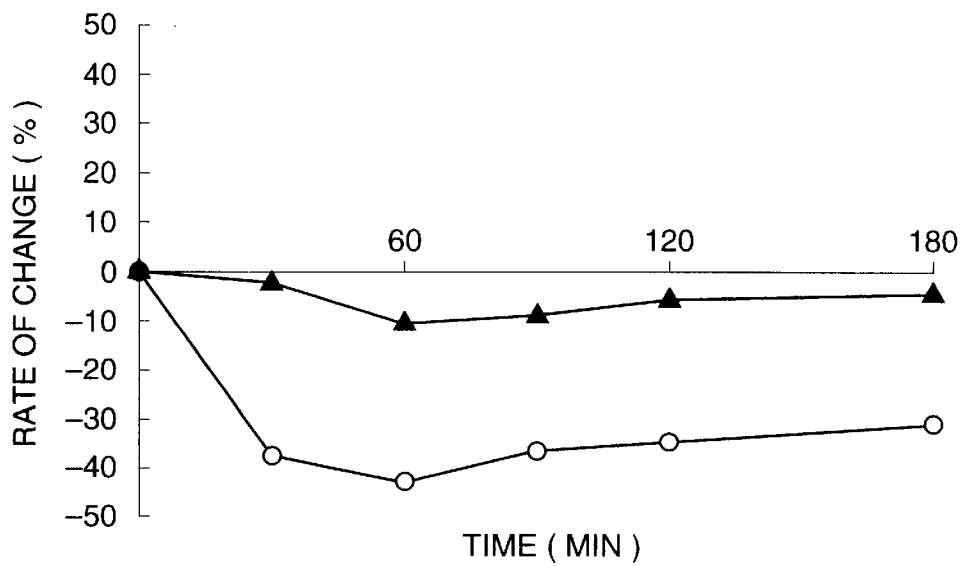
Figure 10:
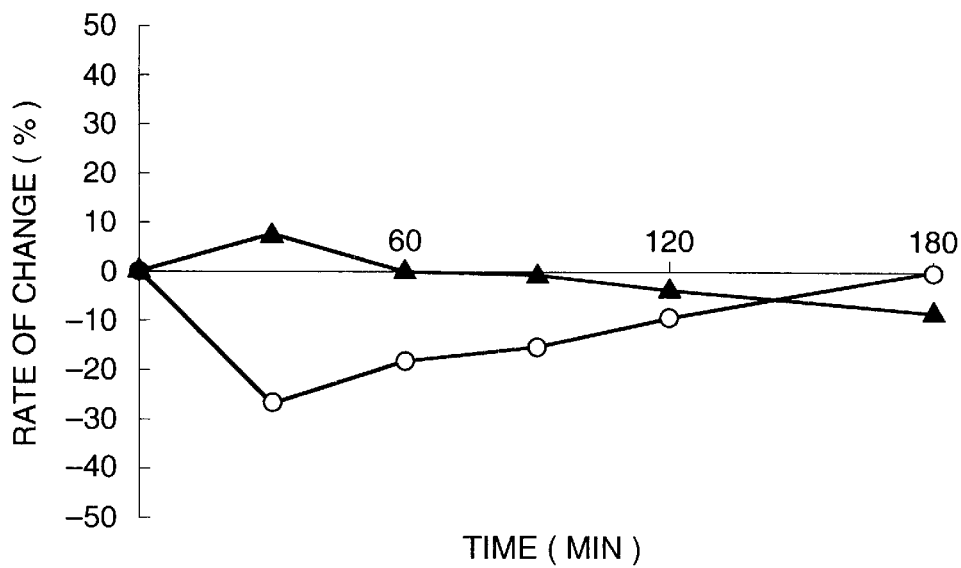

FIGS. 1 to 10 show changes of the concentrations of glucose and 3-hydroxybutyric acid in blood, which are expressed as rates of change from the values before the administration (FIG. 1: water for injection, FIG. 2: 1 mmol/kg of glucose, FIG. 3: 1 mmol/kg of alanine, FIG. 4: 2 mmol/kg of alanine, FIG. 5: 1 mmol/kg of glutamine, FIG. 6: 1 mmol/kg of glutamic acid, FIG. 7: 1 mmol/kg of valine, FIG. 8: 2 mmol/kg of valine, FIG. 9: 2 mmol/kg of isoleucine, FIG. 10: 2 mmol/kg of serine). In the figures, the symbols "-○-" and "-▲-" correspond to the rates of change of 3-hydroxybutyric acid and glucose, respectively. As shown in the figures, valine, isoleucine and serine reduced the concentration of ketone bodies without largely increasing the concentration of glucose in blood, and therefore, they were found to be effective as ketosis-treating agents with no increase of a blood glucose value and extremely little influence on glucose metabolism.

Furthermore, as shown in the figures, the effect on reduction of ketone bodies disappeared within about 4 hours when glucose was used. On the other hand, when glutamine, glutamic acid, valine or isoleucine was used, the period of effecting the reduction of the concentration of ketone bodies was expected to be 24 hours or more, and therefore, they were effective as ketosis-treating agents having long duration of the effect.

EXAMPLES 2

Effects at Intravenous Administration

Wistar male rats of 6 to 8 week age were subjected to ketosis under starvation for 48 hours and then used for the experiment. Each of glutamine and isoleucine was dissolved in water for injection and administered into a tail vein to give a dose of 3 mmol/kg-body weight. As controls, the same quantity of physiological saline was similarly administered, or each of glucose, xylitol, and alanine was similarly administered to give a dose of 3 mmol/kg-body weight.

Before the administration, and 15, 30, 60, 120, 180, and 240 minutes after the administration, blood was collected from a tail vein and the concentration of 3-hydroxybutyric acid was measured.

Figure 11:
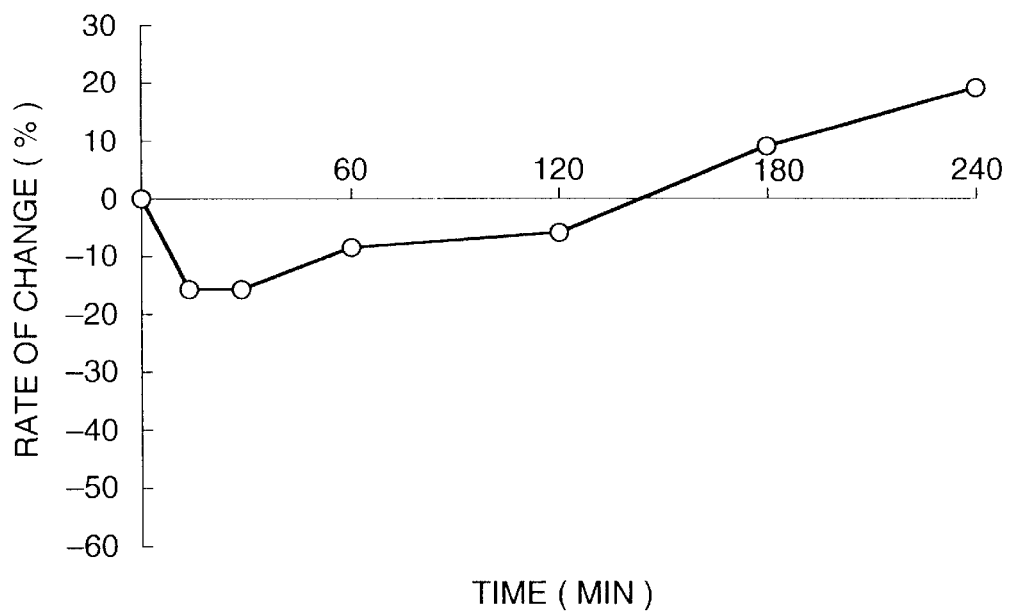
FIGS. 11 to 16 show changes of the concentration of 3-hydroxybutyric acid in blood in Example 2.
Figure 12:
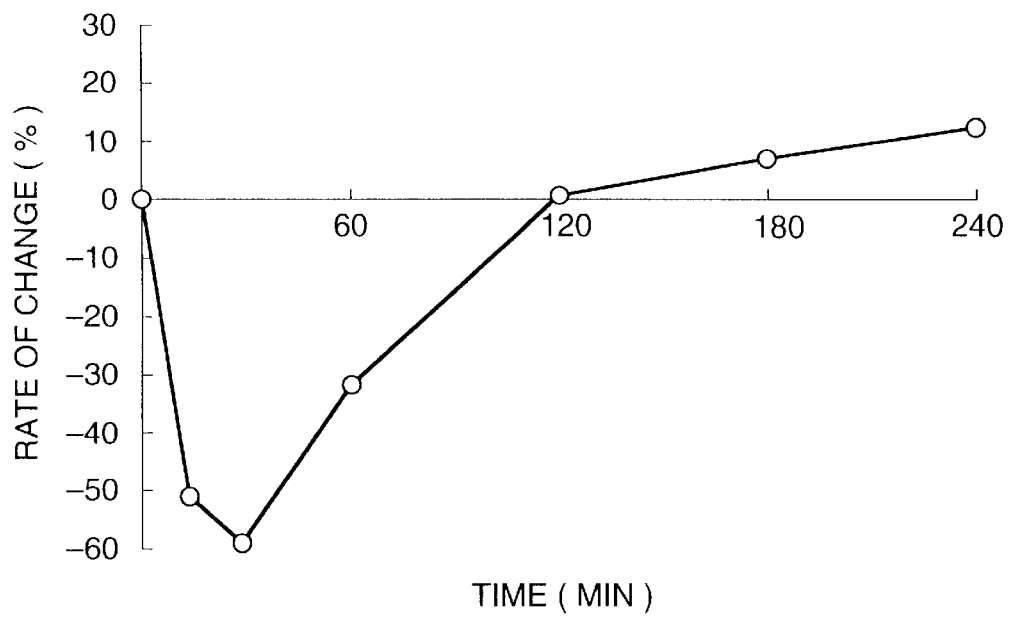
Figure 13:
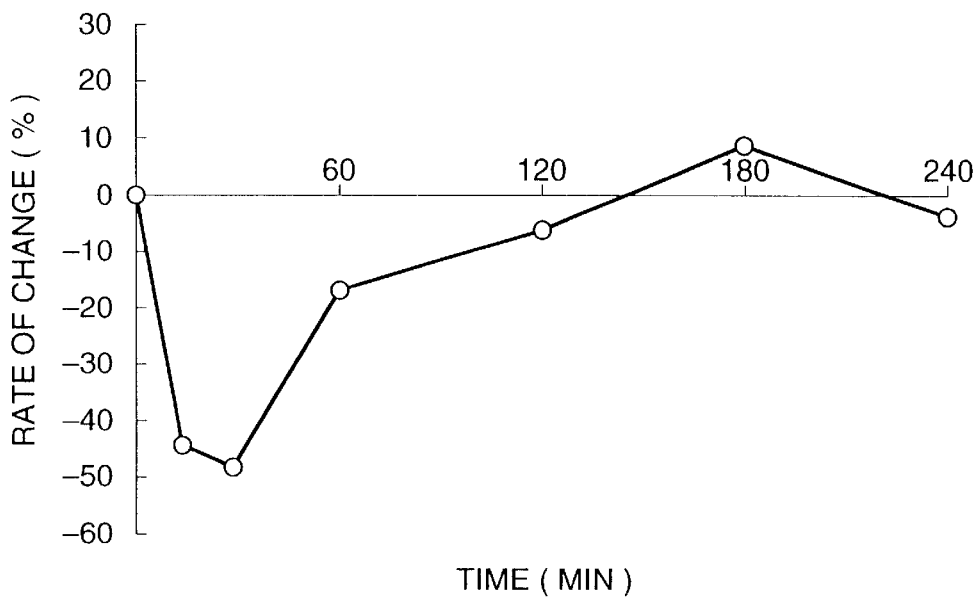
Figure 14:
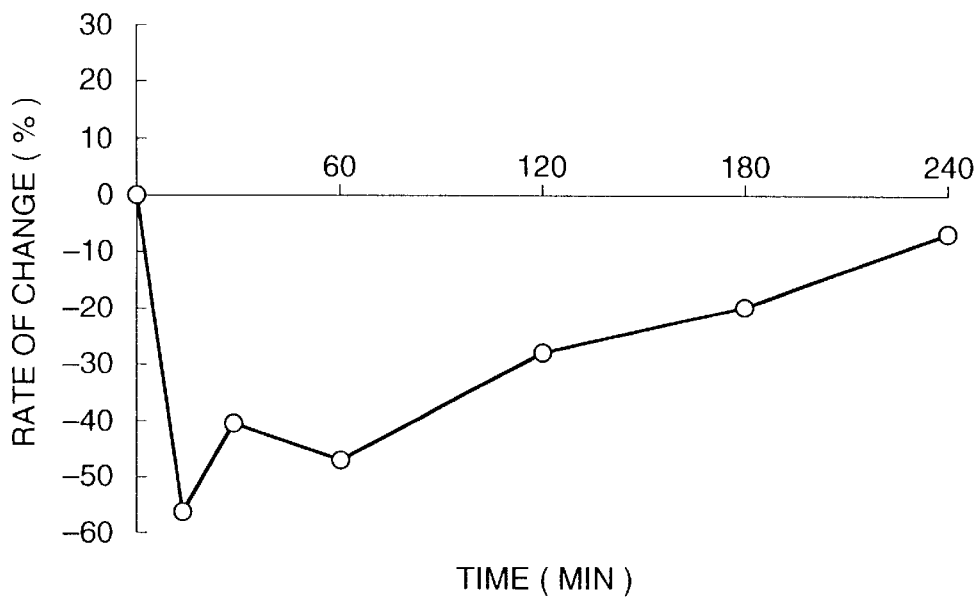
Figure 15:
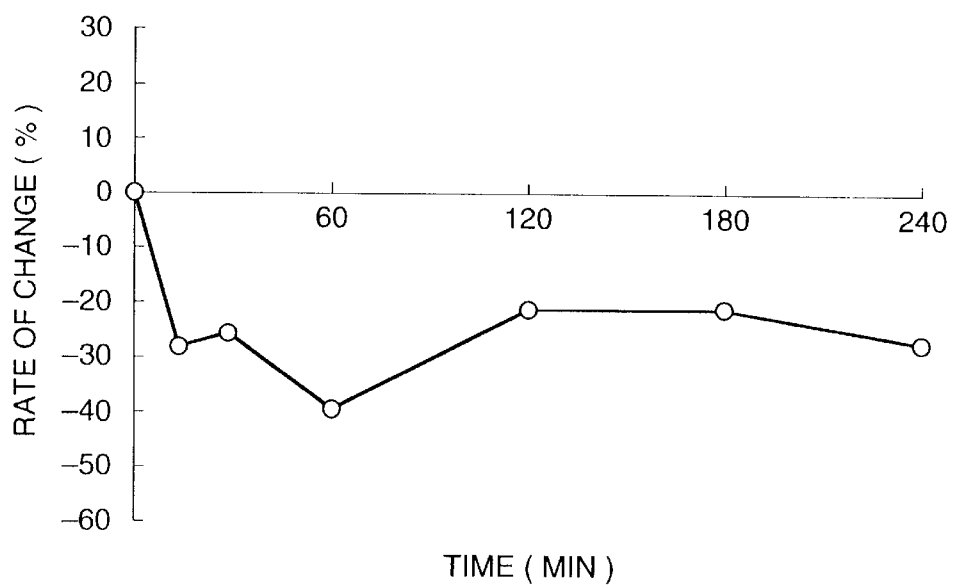
Figure 16:
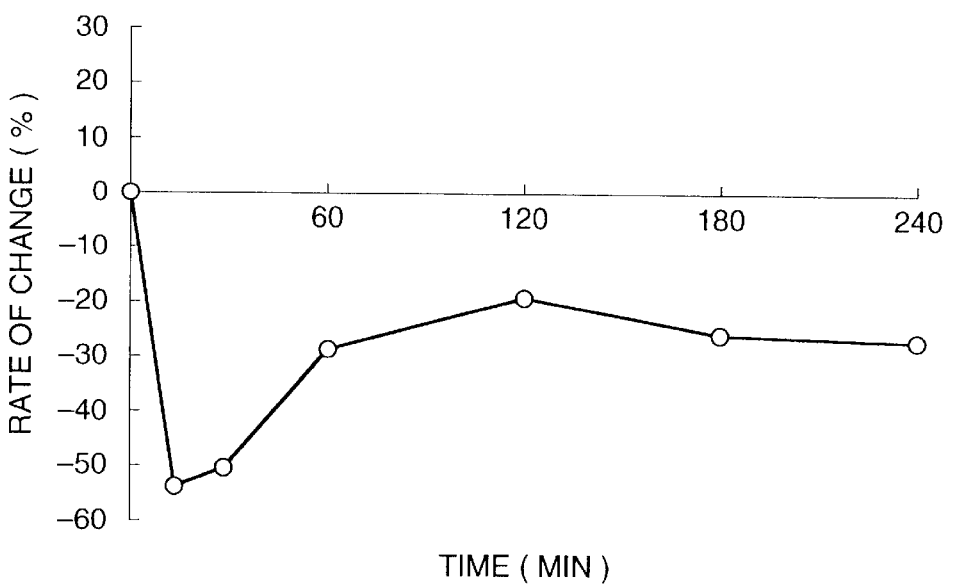

FIGS. 11 to 16 show changes of the concentration of 3-hydroxybutyric acid expressed as rates of change from the value before the administration (FIG. 11: physiological saline, FIG. 12: 3 mmol/kg of glucose, FIG. 13: 3 mmol/kg of xylitol, FIG. 14: 3 nmmol/kg of alanine, FIG. 15: 3 mmol/kg of glutamine, FIG. 16: 3 mmol/kg of isoleucine). In the figures, the symbol "-○-" corresponds to the rate of change of 3-hydroxybutyric acid. As shown in the figures, when glucose was used, the effect on reducing ketone bodies disappeared within 2 hours. On the other hand, when glutamine or isoleucine was used, the period of effecting the reduction of the concentration of ketone bodies was expected to be 24 hours or more, and thus, they were effective as ketosistreating agents having long duration of the effect.

This application is based on Japanese applications No. Hei 11-294931 filed on Oct. 18, 1999, the entire content of which is incorporated hereinto by reference.

While the invention has been described in detail and with reference to specific embodiments thereof, it will be apparent to one skill in the art that various changes and modifications can be made therein without departing from the spirit and scope thereof.

What is claimed is:

1. A method for treating ketosis, comprising administering to a human or animal an effective amount of a composition comprising at least one amino acid selected from the group consisting of valine, isoleucine, and serine, wherein said amino acid is administered in an amount of 20 to 500 mg per kg body weight effective to reduce ketone bodies, and wherein said composition is administered intravenously, and wherein said ketosis is caused by diabetes.

2. The method of claim 1, wherein said amino acid is selected from the group consisting of valine and isoleucine.

3. A method for treating a symptom related to ketone bodies, comprising administering to a human or animal an effective amount of a composition comprising at least one amino acid selected from the group consisting of valine, isoleucine, and serine, wherein said amino acid is administered in an amount of 20 to 500 mg per kg body weight effective to reduce ketone bodies, wherein said composition is administered intravenously, wherein said symptom is selected from the group consisting of hepatophosphorylase deficiency, acetonemic vomiting, fructose-bisphosphatase deficiency, congenital disorders of organic acid metabolism, and 3-ketoacid-CoA transferase deficiency, and wherein said symptom related to ketone bodies is caused by diabetes.

4. The method of claim 3, wherein said amino acid is selected from the group consisting of valine and isoleucine.

* * * * *